US006187931B1

(12) United States Patent
Belmont et al.

(10) Patent No.: US 6,187,931 B1
(45) Date of Patent: Feb. 13, 2001

(54) PROCESS FOR MAKING FLUOROPHTHALIMIDES

(75) Inventors: Stephen E. Belmont; Charles R. Everly; Yunqi Liu, all of Baton Rouge, LA (US)

(73) Assignee: Albemarle Corporation, Richmond, VA (US)

(*) Notice: Under 35 U.S.C. 154(b), the term of this patent shall be extended for 0 days.

(21) Appl. No.: 09/287,153

(22) Filed: Apr. 6, 1999

(51) Int. Cl.$^7$ .................................................. C07D 209/48
(52) U.S. Cl. .............................................................. 548/480
(58) Field of Search .............................................. 548/480

(56) References Cited

U.S. PATENT DOCUMENTS

| | | | |
|---|---|---|---|
| 4,069,262 | 1/1978 | Kunz | 260/646 |
| 4,287,374 | 9/1981 | North | 568/937 |
| 4,642,399 | 2/1987 | White | 568/938 |
| 4,769,493 | 9/1988 | Ito et al. | 562/480 |
| 4,849,552 | 7/1989 | Cantrell | 58/937 |
| 4,925,966 | 5/1990 | Kobayashi et al. | 558/419 |
| 4,990,661 | 2/1991 | Peterson et al. | 562/493 |
| 4,996,355 | 2/1991 | Gurusamy | 562/493 |
| 5,047,553 | 9/1991 | Nowak et al. | 548/476 |
| 5,179,230 | 1/1993 | Papenfuhs et al. | 562/493 |
| 5,196,590 | 3/1993 | Oi et al. | 562/493 |
| 5,523,476 | 6/1996 | Seki et al. | 562/479 |
| 5,596,104 | 1/1997 | O'Reilly et al. | 548/480 |
| 5,599,980 | 2/1997 | Marhold et al. | 562/840 |
| 5,648,504 | 7/1997 | Seki et al. | 549/246 |

OTHER PUBLICATIONS

Kumai et al., Chemical Abstracts, 113:152040, 1990.*

Smyth et al., "Inexpensive, Active KF for Nucleophilic Aromatic Displacement Reactions", Tetrahedron, vol. 51, No. 22, 1995, pp. 6363–6376.

Chen et al., "Preparation of 2,3,4,5–Tetrafluorobenzoic Acid" Chinese Journal of Pharmaceuticals, 1994, vol. 25, Issue 8, pp. 360–362 (5 pages translated).

O'Reilly, Neil J., et al., "An Expedient Route to the Quinolone Antibacterial Intermediate, 2,4,5–Trifluorobenzoic Acid", Syn. Lett., Oct. 1990, pp. 609–610.

Rosen et al., "Tetrachloroisoindolines and Related Systems. Alkylation Reactions and Inductive Effects", J. Am. Chem. Soc., vol. 79, 1957 pp. 3167–3174.

Fuller, "Preparation of Polyfluoroaromatic Compounds by the Reaction of Perhalogeno–aromatic Compounds with Potassium Fluoride in Sulpholan", Journal Chem. Soc., 1965, pp. 6264–6267.

Fertel, "Process Improvements in the Synthesis of 2,4, 5–Trifluorobenzoic Acid. Selective Hydrodefluorination of Tetrafluorophthalimides", Organic Process Research & Development, 1998, vol. 2, pp. 111–115.

Hirusawa et al., "Neue Synthetische Methode von Tetraphenyl–Phosphoniumhalogeniden", Bulletin of Chem. Soc. Japan, 1957, vol. 30, No. 6, pp. 667–670 (not translated).

Suzuki et al., "General and Highly Efficient Syntheses of m–Fluoro Arenes Using Potassium Fluoride–Exchange Method", Bulletin of the Chem. Soc. Of Japan, 1990, vol. 63, No. 7, pp. 2010–2017.

Ishikawa et al., "Enhanced Effect of Spray–Dried Potassium Fluoride on Fluorination", Chemistry Letters, The Chem. Soc. Of Japan, 1981, pp. 761–764.

Kimura et al., "Freeze–Dried Potassium Fluoride: Synthetic Utility As A Fluorinating Agent", Tetrahedron Letters, 1989, vol. 30, No. 10, pp. 1271–1272.

* cited by examiner

Primary Examiner—Fiona T. Powers
(74) Attorney, Agent, or Firm—Philip M. Pippenger

(57) ABSTRACT

Tri- or tetrafluorophthalimides are produced in a halogen-exchange reaction utilizing a metal fluoride salt and a dihydrocarbyl sulfoxide as the solvent. No phase-transfer catalyst is employed. The process has been found capable of producing the fully fluorinated phthalimide in yields of over 90% GC in reactions performed at 135–155 ° C. in reaction periods of as little as one hour even though no phase-transfer catalyst is employed.

27 Claims, No Drawings

PROCESS FOR MAKING FLUOROPHTHALIMIDES

TECHNICAL FIELD

The subject of this invention is a high-yield halogen-exchange fluorination reaction which can convert tri- and tetrahalophthalimides in which at least one phthalimide aromatic ring substituent is a non-fluorine halogen into fully-exchanged tri- and tetrafluorophthalimides.

BACKGROUND

The substitution of fluorine for chlorine or another halogen atom at an aromatic carbon of a tri- or tetrahalophthalimide is an integral reaction in the production of many widely used organic compounds. As such, it is a reaction of considerable commercial importance. For example, the conversion of N-methyltetrachlorophthalimide to N-methyltetrafluorophthalimide is an important step in the production of compounds in the Floxacin family of antibiotics, a commonly prescribed, commercially successful group of synthetic drugs.

A problem typically encountered with halogen-exchange fluorination is the propensity for the formation of products in which at least one aromatic carbon remains substituted by a non-fluorine halogen atom. For example, the halogen-exchange fluorination of a tetrachlorinated phthalimide substrate can lead to mono-, di- and trifluorinated products in addition to the tetrafluorinated product, often the desired end product of the reaction. This tendency towards incomplete halogen-exchange fluorination of halophthalimides generally has the effect of reducing the purity and yield of the fully-exchanged product. In particular, the fluorination of tetrachlorophthalimides, typically carried out with a metal fluoride salt in solvents such as sulfolane, often produces substantially only partially-exchanged products, especially when conducted at moderate temperatures such as those in the range of 150° C.

In order to increase the proportion of the fully-exchanged phthalimide, the reaction is often run at temperatures in excess of 200° C., and for durations of ten hours or more. Unfortunately, such high temperatures and long reaction times are often of limited effectiveness, as such conditions can ultimately result in degradation of the phthalimide moiety. In order to allow the use of conditions which are less harsh, it is typical to perform the reaction in the presence of a phase-transfer catalyst.

However, many phase-transfer catalysts can be extremely costly. It is not unusual for the small amount of phase-transfer catalyst utilized to cost more than any other chemical component of the reaction. A further disadvantage associated with these catalysts is that further processing of even residual amounts of phase-transfer catalyst can result in the formation of tarry impurities due to polymerization of the catalyst. Thus, once halogen-exchange fluorination has been conducted, it is often necessary to resort to purification techniques in order to separate the catalyst from the desired product.

A multiple extraction procedure is typically performed to accomplish this end. Unfortunately, extraction and other methods which can be used to remove the catalyst from the reaction mixture following halogen-exchange fluorination can reduce the yield of the desired product and complicate the reaction work-up. Another problem created by the addition of extraction steps to the synthesis is the increased difficulty in recycling solvents due to contamination with extractant reagents. Recycling can be particularly important if the solvent is costly, as in the case of one commonly used solvent, sulfolane. For example, in the event that sulfolane and water were used as solvent and extractant, respectively, the sulfolane would typically need to be dried before reuse.

It would represent a significant advance in the state of the art if a method of halogen-exchange fluorination of tri- and tetrahalophthalimides which contain non-fluorine halogens could be found which can achieve a high yield and rate of production of fully-exchanged product while eliminating the expense, multiple extractions, and solvent recycling problems associated with phase-transfer catalysts.

SUMMARY OF THE INVENTION

A process has been discovered which can provide for high yield and production rate of fully-exchanged, tri- and tetrafluorophthalimides while eliminating the detriments associated with the use of phase-transfer catalysts. It has been found that when the halogen-exchange fluorination of tri- and tetrahalophthalimides, such phthalimides having at least one aromatically substituted non-fluorine halogen atom, is carried out in a sulfoxide solvent at a range of moderate temperatures, omission of the phase-transfer catalyst can actually increase product yield and rate of accumulation with respect to the reaction performed under identical reaction conditions, but in the presence of the phasetransfer catalyst.

Accordingly, this invention provides, inter alia, a process for producing tri- or tetrafluoroaromatics, which process comprises:

a) forming a phase-transfer catalyst-free reaction mixture comprised of (1) a tri- or tetrahalophthalimide in which at least one aromatic carbon atom in the molecule, and preferably in which each of at least three aromatic carbon atoms in the molecule, is substituted by a non-fluorine halogen atom, (2) a metal fluoride salt, and (3) an inert hydrocarbyl sulfoxide solvent; and b) maintaining said mixture at one or more temperatures in the range of about 135° C. to about 185° C. such that a compound is formed in which each non-fluorine halogen atom of the halophthalimide which is attached to an aromatic carbon atom is replaced by a fluorine atom.

The process of this invention is particularly efficacious when carried out at temperatures in the range of about 135° C. to about 155° C. In a particularly preferred embodiment, 3,4,5,6-tetrachlorophthalimides, especially N-methyl tetrachlorophthalimide is heated with an alkali metal fluoride salt, most preferably potassium fluoride, in dimethyl sulfoxide.

The above and other embodiments will be apparent from the ensuing description and appended claims.

FURTHER DESCRIPTION OF THE INVENTION

The phthalimides used in conducting the process of this invention are tri- or tetrahalophthalimides, e.g. phthalimides which are halogenated in three or four of the following aromatic ring positions: 3, 4, 5 or 6, at least one of said positions being substituted by a halogen other than fluorine. If a trihalophthalimide is utilized, the aromatic ring position which is not substituted by a halogen atom or the imide moiety can be occupied by a substituent which does not impair the ability of the compound to undergo fluorination at the aromatic ring sites occupied by non-fluorine halogens. Carbonyl, cyano, nitro, and other such substituents are permissible. The phthalimide nitrogen can be unsubstituted, or it can bear substituent groups such as alkyl, alkylaryl, alkoxy, hydroxyl, cyano, carboxyl, ester, keto, amino, nitro, sulfonyl, or others which do not impair the ability of the phthalimide to undergo fluorination of the aromatic ring at sites occupied by non-fluorine halogens. Examples of such halophthalimides are 3,4,5,6-tetrabromo-N-hexadecylphthalimide and 3,4,5,6-tetraiodo-N-tetradecylphthalimide. Preferred are tri- and tetrachlorophthalimides. Examples of such are 3,4,5-trichlorophthalimide, 3,4,6-trichlorophthalimide, 3,4,5,6-tetrachloro-N-phenylphthalimide, 3,4,5,6-tetrachloro-N-isobutyl-phthalimide and 3,4,5,6-tetrachloro-N-[2-(diethylamino)ethyl]phthalimide. More preferred are the tetrachlorophthalimides, examples of such being 3,4,5,6-tetrachloro-N-phenyl phthalimide, 3,4,5,6-tetrachloro-N-methylphthalimide, with the latter being the most preferred reactant.

The above phthalimides can be synthesized by methods such as conversion of the corresponding phthalic anhydride to an imide by heating with an amine. The desired aromatic ring substituency can often be imparted to phthalic anhydride prior to imide formation reaction.

Preferably, an alkali metal fluoride salt, an alkaline earth metal fluoride salt or other metal fluoride salt is used as a fluorination agent. Suitable examples include lithium fluoride, sodium fluoride, potassium fluoride, rubidium fluoride, cesium fluoride, magnesium fluoride, calcium fluoride, silver fluoride and the like. More preferably, the fluorinating agent is sodium fluoride or potassium fluoride. Most preferably, the fluorinating agent is potassium fluoride.

To enhance its reactivity, the metal fluoride salt should be in finely-divided or powdery anhydrous form. One convenient way of ensuring that the metal fluoride is suitably anhydrous is to form a slurry of powdery metal fluoride salt in a suitable volatile hydrocarbon such as benzene that forms an azeotrope with water, and heat the mixture to dryness, while of course suitably handling and disposing of the vapors. A particularly useful form of alkali metal fluoride for use in the process may be produced by utilizing the procedure described by T. P. Smyth, A. Carey and B. K. Hodnett in *Tetrahedron*, Volume 51, No. 22, pp. 6363–6376 (1995). In brief, their described procedure involves recrystallizing KF from a methanol solution by slow evaporation of the solvent, followed by drying at 100° C. Other suitable activated forms include spray dried alkali metal fluorides (see N. Ishikawa, et al. *Chem. Letts*, 1981, 761), and freeze dried alkali metal fluorides (see Y. Kimura, et al. *Tetrahedron Letters*, 1989, 1271).

A sulfoxide solvent is used in the process of this invention. Although it is preferable to utilize sulfoxide solvents which are liquids at room temperature as well as at reaction temperatures, sulfoxide solvents which are solid at room temperature and liquid at reaction temperature can also be used. Preferably, a sulfoxide which has a carbon atom content of up to about fourteen carbon atoms in the molecule is utilized as a solvent. Suitable examples include the following: dibenzyl sulfoxide, di-n-butyl sulfoxide, di-n-propyl sulfoxide, di-phenyl sulfoxide, p-tolyl sulfoxide, diisobutyl sulfoxide, and similar solvents. More preferably, a sulfoxide which has a carbon atom content of up to about six carbon atoms in the molecule is utilized as a solvent. Examples of such include diethyl sulfoxide, tetramethylene sulfoxide and dimethyl sulfoxide. It is most preferable to use dimethyl sulfoxide as a solvent. In the above listing of sulfoxide solvents, the convention of dropping the di- prefix (e.g. ethyl sulfoxide instead of diethyl sulfoxide) is not used.

Typically, the mole ratio of halophthalimide to sulfoxide is in the range of about 0.02 mole of halophthalimide per mole of sulfoxide to about 0.20 moles of halophthalimide per mole of sulfoxide. Preferably the mole ratio is in the range of about 0.04 moles of halophthalimide per mole of sulfoxide to about 0.10 moles of halophthalimide per mole of sulfoxide. A mole ratio of about 0.06 moles of halophthalimide per mole of sulfoxide is most preferred.

In order to form fully-exchanged tri- or tetrafluorophthalimides in high yields, it is preferable to utilize the metal fluoride salt and the halophthalimide in mole ratios such that, there are from 1 to 2 atoms of fluorine as fluorinating agent per each non-fluorine halogen atom on the aromatic ring of the phthalimide moiety of the tri- or tetrahalophthalimide. For example, if trichlorophthalimide is being fluorinated, one should employ an amount of fluorinating agent that would provide from 3 to 6 atoms of fluorine per molecule of trichlorophthalimide. Preferably, the amount of fluorinating agent used is equivalent to from about 1.13 to about 1.50 atoms of fluorine per each non-fluorine halogen atom on the aromatic ring of the phthalimide moiety of the tri- or tetrahalophthalimide. A ratio of about 1.25 atoms of fluorine per each such non-fluorine halogen atom is most preferred.

It is desirable to heat the reaction mixture to a temperature in the range of about 135° C. to about 185° C. Temperatures in the range of about 135° C. to about 155° C. are preferred in as much as the reaction rates when practicing this invention in this temperature range are rapid and minimal decomposition of the desired product is incurred.

The reaction mixture can be formed in many ways. The metal fluoride salt and the halophthalimide can be added to the solvent simultaneously or in either order. Alternatively, if desired, the solvent can be added to a preformed mixture of the metal fluoride salt and the halophthalimide. It is also permissible to add one reactant to a mixture of the remaining reactant and the solvent. The process of this invention can be conducted as a batch process, a semi-continuous process, or a continuous process. As an example of the latter, a preformed reaction mixture is continuously introduced into and passed through a heated reaction zone, and the reaction product is continuously withdrawn from the reaction zone, typically at a rate such that the level of the reaction product in the reaction zone remains substantially constant throughout the entire reaction. Residence times of the reactants in the heated reaction zone will be sufficient to effect the requisite exchange of aryl fluorine atoms for non-fluorine aryl halogen atoms.

The application of heat to the reaction can be accomplished in many ways. The reaction mixture can be preformed and subsequently heated. If desired, a preformed reaction mixture can be continuously passed through a heated reaction zone, as indicated above. The reactant flow rate through this zone, as well as the temperature of the zone can be adjusted to maximize product yield. Thus, staged heating of the reactants in a reaction zone can be employed. Still another way of applying heat to the reaction mixture involves heating a mixture of the solvent and the halophthalimide or the metal fluoride salt, followed by the addition of the remaining reaction components. Thus, in general, heat can be applied at any stage of reaction mixture formation, i.e., before, during, or after the formation of the reaction mixture.

A highly advantageous feature of this invention is that a high yield of the desired product can be formed in extremely short reaction periods even though no catalyst is employed and even though extremely high reaction temperatures are not used. Although the time in which a given yield can be achieved depends in part upon the identity of halophthalimide reactant used, a yield of at least 80% GC in a reaction period of two hours or less is readily achieved in the practice of this invention. In fact, this invention makes it possible to achieve yields as high as 90% GC and above in two hours or less when utilizing preferred reaction conditions of this invention. Indeed, it has been found possible to produce the desired product in yields of 90% GC or above even in reaction periods as short as one hour using reaction temperatures in the range of about 135° to about 155° C.

The reaction mixture is formed and the reaction is performed in an anhydrous atmosphere of inert gas, such as nitrogen, argon, krypton, or xenon. Additionally, such precautions can aid in maintaining a relatively low water content in the reaction mixture.

Preferably the reaction is preformed while suitably agitating the reaction mixture. Thus the reactor is typically equipped with a stirrer or use is made of a rocking autoclave, shaker or other means of mixing or agitating the reaction mixture so that the metal fluoride salt and the halophthalimide remain in intimate contact with each other during the course of the reaction.

After formation, the fluoroaromatic compounds can be separated from the reaction mass by distillation, extraction, evaporation, or other separation methods.

The following examples are presented for purposes of illustration, and are not intended to limit, and should be construed as limiting, the scope of this invention. The examples illustrate the high yield of fully-exchanged product obtainable at short reaction times and in the absence of a phase-transfer catalyst when a sulfoxide solvent is used.

EXAMPLE 1

N-methyltetrachlorophthalimide (5.0 g, 16.7 mmol) and spray-dried potassium fluoride (5.0 g, 84 mmol) were added to an oven-dried 100-mL 3-neck RB flask, with condenser and thermocouple attached, in a nitrogen purgebox. The apparatus was transferred to a hood and put under nitrogen overpressure. Anhydrous DMSO (35 mL) was added via a syringe, and the reaction was heated to 140° C. After 1 hour, there was an 85.8% GC conversion to N-methyltetrafluorophthalimide. After 2 hours, there was a 93.0% GC conversion to N-methyltetrafluorophthalimide.

EXAMPLE 2

N-methyltetrachlorophthalimide (5.0 g, 16.7 mmol) and spray-dried potassium fluoride (5.0 g, 84 mmol) were added to an oven-dried 100-mL 3-neck RB flask, with condenser and thermocouple attached, in a nitrogen purgebox. The apparatus was transferred to a hood and put under nitrogen overpressure. Anhydrous DMSO (35 mL) was added via a syringe, and the reaction was heated to 150° C. After 1 hour, there was a 94.4% GC conversion to N-methyltetrafluorophthalimide.

The following comparative example illustrates the poor yield of fully-exchanged product obtained in the absence of a phase-transfer catalyst when sulfolane is utilized instead of a sulfoxide solvent.

COMPARATIVE EXAMPLE 1

N-methyltetrachlorophthalimide (5.0 g, 16.7 minol) and spray-dried potassium fluoride (5.0 g, 84 mmol) were added to an oven-dried 100-mL 3-neck RB flask, with condenser and thermocouple attached, in a nitrogen purgebox. The apparatus was transferred to a hood and put under nitrogen overpressure. Anhydrous sulfolane (35 mL) was added via a syringe, and the reaction was heated to 140° C. After 2 hours, there was a 0% GC conversion to N-methyltetrafluorophthalimide. After 1 hour at 150° C., there was a 0.4% GC conversion to N-methyltetrafluorophthalimide.

The following comparative example illustrates the lack of yield enhancement of fully-exchanged product in the absence of a phase-transfer catalyst when a sulfoxide solvent is used and the reaction is conducted at a temperature outside the range of about 135° C. to about 185° C.

COMPARATIVE EXAMPLE 2

N-methyltetrachlorophthalimide (5.0 g, 16.7 mmol) and spray-dried potassium fluoride (5.0 g, 84 mmol) were added to an oven-dried 100-mL 3-neck RB flask, with condenser and thermocouple attached, in a nitrogen purgebox. The apparatus was transferred to a hood and put under nitrogen overpressure. Anhydrous DMSO (35 mL) was added via a syringe, and the reaction was heated to 130° C. After 3 hours, there was a 79.4% GC conversion to N-methyltetrafluorophthalimide. After 5 hours, there was a 90.8% GC conversion to N-methyltetrafluorophthalimide.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient just as it existed at the time just before it was first contacted, blended or mixed with one or more other substances, components and/or ingredients in accordance with the present disclosure. Thus the fact that a substance, component or ingredient may have lost its original identity through a chemical reaction or transformation through the course of contacting, blending or mixing operations, if conducted in accordance with this disclosure and with the application of common sense and the ordinary skill of a chemist, is wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises:
    a) forming a phase-transfer catalyst-free reaction mixture comprised of (1) a tri- or tetrahalophthalimide in which at least one aromatic carbon atom in the molecule is substituted by a non-fluorine halogen atom, (2) a metal fluoride salt, (3) an inert hydrocarbyl sulfoxide solvent; and b) maintaining said mixture at one or more temperatures in the range of about 135° C. to about 185° C. such that a compound is produced in which each non-fluorine halogen of the halophthalimide of a) which is attached to an aromatic carbon atom is replaced by a fluorine atom.

2. A process as in claim 1 wherein (3) is dimethyl sulfoxide.

3. A process as in claim 1 wherein the temperature in b) is in the range of about 135° C. to about 155° C.

4. A process as in claim 1 wherein (2) is potassium fluoride or sodium fluoride.

5. A process as in claim 1 wherein (2) is spray-dried finely-divided potassium fluoride or spray-dried finely-divided sodium fluoride.

6. A process as in claim 1 wherein the fluorophthalimide in b) is produced in a yield of at least about 80% GC, based on the initial molar quantity of said tri- or tetrahalophthalimide, in a reaction period of up to about two hours.

7. A process as in claim 1 wherein (2) is potassium fluoride or sodium fluoride, wherein (3) is dimethyl sulfoxide, and wherein the temperature in b) is in the range of about 135° C. to about 155° C.

8. A process as in claim 7 wherein fluorophthalimide in b) is produced in a yield of at least about 90% GC, based on the initial molar quantity of said tri- or tetrahalophthalimide, in a reaction period of up to about two hours.

9. A process as in claim 1 wherein said tri- or tetrahalophthalimide is characterized in that each of at least three aromatic carbon atoms in the molecule is substituted by a non-fluorine halogen atom.

10. A process as in claim 1 wherein (1) is a tetrachlorophthalimide.

11. A process as in claim 10 wherein (3) is dimethyl sulfoxide.

12. A process as in claim 10 wherein the temperature in b) is in the range of about 135° C. to about 155° C.

13. A process as in claim 10 wherein (2) is potassium fluoride or sodium fluoride.

14. A process as in claim 10 wherein (2) is spray-dried finely-divided potassium fluoride or spray-dried finely-divided sodium fluoride.

15. A process as in claim 10 wherein the fluorophthalimide in b) is produced in a yield of at least about 80% GC, based on the initial molar quantity of the tetrachlorophthalimide, in a reaction period of up to about two hours.

16. A process as in claim 10 wherein (2) is potassium fluoride or sodium fluoride, wherein (3) is dimethyl sulfoxide, and wherein the temperature in b) is in the range of about 135° C. to about 155° C.

17. A process as in claim 16 wherein tetrafluorophthalimide in b) is produced in a yield of at least about 90% GC, based on the initial molar quantity of said tetrachlorophthalimide, in a reaction period of up to about two hours.

18. A process as in claim 10 wherein said tetrachlorophthalimide is 3,4,5,6-tetrachloro-N-methylphthalimide, wherein (2) is potassium fluoride or sodium fluoride, wherein (3) is dimethyl sulfoxide, and wherein the temperature in b) is in the range of about 135° C. to about 155° C.

19. A process as in claim 18 wherein 3,4,5,6-tetrafluoro-N-methylphthalimide in b) is produced in a yield of at least about 90% GC, based on the initial molar quantity of 3,4,5,6-tetrachloro-N-methylphthalimide, in a reaction period of no more than about one hour.

20. A process as in claim 19 wherein (3) is spray-dried finely-divided potassium fluoride.

21. A process which comprises heating a reaction mixture formed from ingredients comprising (1) a tri- or tetrahalophthalimide in which at least one aromatic carbon atom is substituted by a non-fluorine halogen atom, (2) a metal fluoride salt, and (3) a hydrocarbyl sulfoxide solvent, said mixture being devoid of a phase-transfer catalyst, at a temperature in the range of about 135° C. to about 185° C. to produce a fluorophthalimide in which each non-fluorine halogen atom of the halophthalimide which is attached to an aromatic carbon is replaced by a fluorine.

22. A process as in claim 21 wherein said temperature is in the range of about 135° C. to about 155° C., wherein said sulfoxide is dimethyl sulfoxide, and wherein said metal fluoride salt is finely-divided potassium fluoride.

23. A process as in claim 22 wherein (1) is a 3,4,5,6-tetrachlorophthalimide.

24. A process as in claim 23 wherein the 3,4,5,6-tetrafluorophthalimide is produced in a yield of at least about 80% GC, based on the initial molar quantity of the 3,4,5,6-tetrachlorophthalimide, in a reaction period of up to about two hours.

25. A process as in claim 22 wherein (1) is a 3,4,5,6-tetrachloro-N-methylphthalimide.

26. A process as in claim 25 wherein the 3,4,5,6-tetrafluoro-N-methylphthalimide is produced in a yield of at least about 90% GC, based on the initial molar quantity of the 3,4,5,6-tetrachlorophthalimide, in a reaction period of up to about two hours.

27. A process as in claim 26 wherein said reaction period is no more than one hour.

* * * * *